United States Patent
Parihar et al.

(10) Patent No.: US 7,217,277 B2
(45) Date of Patent: May 15, 2007

(54) DEVICE FOR PROVIDING INTRACARDIAC ACCESS IN AN OPEN CHEST

(75) Inventors: Shailendra K. Parihar, Coopersburg, PA (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 623 days.

(21) Appl. No.: 10/261,429

(22) Filed: Sep. 30, 2002

(65) Prior Publication Data

US 2004/0092984 A1    May 13, 2004

(51) Int. Cl.
*A61B 17/32* (2006.01)
(52) U.S. Cl. .................................. 606/167; 607/174
(58) Field of Classification Search .............. 604/93, 604/164, 174; 606/144, 167, 191, 213, 215
See application file for complete search history.

(56) References Cited

U.S. PATENT DOCUMENTS

| | | | |
|---|---|---|---|
| 4,423,730 A | 1/1984 | Gabbay | |
| 5,209,737 A | 5/1993 | Ritchart et al. | |
| 5,242,457 A | 9/1993 | Akopov et al. | |
| 5,261,459 A * | 11/1993 | Atkinson et al. | 137/846 |
| 5,308,336 A | 5/1994 | Hart et al. | |
| 5,385,553 A | 1/1995 | Hart et al. | |
| 5,411,491 A * | 5/1995 | Goldhardt et al. | 604/247 |
| 5,720,730 A * | 2/1998 | Blake, III | 604/167.02 |
| 5,810,721 A | 9/1998 | Mueller et al. | |
| 5,829,447 A * | 11/1998 | Stevens et al. | 128/898 |
| 6,010,531 A | 1/2000 | Donlon et al. | |
| 6,079,414 A | 6/2000 | Roth | |
| 6,328,757 B1 | 12/2001 | Matheny | |
| 6,443,957 B1 | 9/2002 | Addis | |
| 6,464,707 B1 | 10/2002 | Bjerken | |
| 6,537,290 B2 | 3/2003 | Adams et al. | |

FOREIGN PATENT DOCUMENTS

| | | |
|---|---|---|
| EP | 1 312 318 A1 | 5/2003 |
| WO | WO 03/034908 A2 | 5/2003 |

* cited by examiner

*Primary Examiner*—Michael J. Hayes
*Assistant Examiner*—Victor Nguyen

(57) ABSTRACT

An access device for providing access into a hollow organ during an open surgical procedure. The access device includes: a body for insertion into an opening in a wall of the hollow organ, the body having a bore for passage of at least a distal portion of an instrument into an interior of the hollow organ; a valve disposed in the bore for allowing passage of the instrument and substantially preventing a fluid in the interior of the hollow organ from leaking outside the hollow organ; and a mechanism for securing the body to the wall of the hollow organ; wherein the body has a low-profile length in an axial direction of the bore.

6 Claims, 7 Drawing Sheets

DEVICE FOR PROVIDING INTRACARDIAC ACCESS IN AN OPEN CHEST

BACKGROUND OF THE INVENTION

1. Field of the Invention

The present invention relates generally to a device for providing access to a hollow organ, and more particularly, to a device for providing intracardiac access in an open chest procedure.

2. Prior Art

Surgery may be performed using open-chest techniques while the heart is under cardioplegic arrest and circulation is maintained by cardiopulmonary bypass. Using such techniques, a gross thoracotomy is created in order to gain access to the heart and great vessels, facilitating clamping and cannulation of the aorta for inducing cardioplegic arrest, and allowing instruments to be introduced into the chest cavity and into the heart to perform a surgical repair. The necessity of stopping the heart significantly heightens the risks attendant such procedures, particularly the risks of causing ischemic damage to the heart muscle, and of causing stroke or other injury due to circulatory emboli produced by aortic clamping and vascular cannulation.

A number of endovascular approaches for use in procedures in which the heart is arrested have been developed in the prior art. These approaches attempt to allow intracardiac access using catheters introduced transluminally from peripheral vessels into the heart. However, these devices suffer from many problems including a lack of control and precise positionability from the proximal ends of the highly flexible and elongated devices, the significant size constraints of peripheral vessels, and the inability to position the devices in all potentially diseased sites within the heart.

A number of minimally invasive or endoscopic access devices for use in beating heart procedures have also been developed in the prior art. These endoscopic devices are used to gain intracardiac access to the heart. Such devices are disclosed in U.S. Pat. No. 6,079,414 to Roth and U.S. Pat. No. 5,829,447 to Stevens et al., which are hereby incorporated by reference. However, such devices generally have a substantially long axial bore into which instruments are passed. The long length of the bore restricts the manipulative capability of the instruments passed through the bore into an interior of the heart. For example, a distal end of the instrument mainly moves in an axial direction and cannot stray very much from a central axis in the axial direction. Furthermore, the instruments must be very straight in order to traverse the long length of the bore, thus, curved instruments cannot be utilized with the endoscopic access devices of the prior art. Lastly, because such endoscopic access devices are directed to the heart wall under observation of a viewing device, they cannot be directly secured to the heart wall to maintain a tight seal against blood flow from the heart.

SUMMARY OF THE INVENTION

Therefore it is an object of the present invention to provide an access device that overcomes the disadvantages of the prior art.

Accordingly, an access device for providing access into a hollow organ during an open surgical procedure is provided. The access device comprising: a body for insertion into an opening in a wall of the hollow organ, the body having a bore for passage of at least a distal portion of an instrument into an interior of the hollow organ; a valve disposed in the bore for allowing passage of the instrument and substantially preventing a fluid in the interior of the hollow organ from leaking outside the hollow organ; and securing means for securing the body to the wall of the hollow organ; wherein the body has a low-profile length in an axial direction of the bore.

Preferably, the hollow organ is a heart.

Preferably, the length of the body in the axial direction of the bore is substantially within a range of 1.5T to 5T, where T is a thickness of the wall.

The valve is preferably a duckbill valve fabricated from an elastomer. Preferably, the elastomer is silicone.

Preferably, the securing means comprises: a lip disposed on a proximal portion of the body; a balloon disposed on a distal portion of the body; and a conduit for supplying a fluid from a fluid source to the balloon for expansion thereof; wherein upon expansion of the balloon, the wall is captured between the lip and the balloon. Preferably, the body, lip, and balloon are cylindrical.

The securing means alternatively comprises: a plurality of hooks movably disposed in the body between exposed and unexposed positions; and actuation means for actuating the plurality of pins from the unexposed position to an exposed position and for embedding the exposed plurality of hooks into the wall. Preferably, the body comprises first and second body portions movable relative to each other and wherein the actuation means comprises: rotatable actuation means for exposing the plurality of hooks upon rotation of one of the first and second body portions relative to the other of the first or second body portions; and translatable actuation means for embedding the exposed plurality of hooks into the wall upon translation of one of the first and second body portions relative to the other of the first or second body portions. The access device preferably further comprises a fluid seal between the first and second body portions.

Also provided is an access device for providing access into a hollow organ during an open surgical procedure. The access device comprising: a body for insertion into an opening in a wall of the hollow organ, the body having a bore for passage of at least a distal portion of an instrument into an interior of the hollow organ; a valve disposed in the bore for allowing passage of the instrument and substantially preventing a fluid in the interior of the hollow organ from leaking outside the hollow organ; a plurality of hooks movably disposed in the body between exposed and unexposed positions; and actuation means for actuating the plurality of pins from the unexposed position to an exposed position and for embedding the exposed plurality of hooks into the wall to secure the body to the wall. Preferably, the hollow organ is a heart.

Preferably, the body comprises first and second body portions movable relative to each other and wherein the actuation means comprises: rotatable actuation means for exposing the plurality of hooks upon rotation of one of the first and second body portions relative to the other of the first or second body portions; and translatable actuation means for embedding the exposed plurality of hooks into the wall upon translation of one of the first and second body portions relative to the other of the first or second body portions. The access device preferably further comprises a fluid seal between the first and second body portions.

Preferably, the body has a low-profile length in an axial direction of the bore to increase a manipulative capability of the instrument through the bore. Preferably, the length of the body in the axial direction of the bore is substantially within a range of 1.5T to 5T, where T is a thickness of the wall.

Preferably, the valve is a duckbill valve fabricated from an elastomer. The elastomer is preferably silicone.

Still yet provided is a method for providing access into an interior of a hollow organ for manipulation of an instrument therein. The method comprises: providing direct access to the hollow organ; making an opening in a wall of the hollow organ; inserting a body of an access device in the opening; securing the body to the wall; passing at least a distal portion of an instrument through a bore in the access device to an interior of the hollow organ; preventing a fluid in the interior of the hollow organ from leaking outside the hollow organ; removing the access device from the opening; and closing the hole in the wall of the internal organ.

Preferably, the closing comprises: providing suturing around a periphery of an area corresponding to the opening prior to making the opening, the suturing having at least two purse strings; and pulling the purse strings to close opening subsequent to the removing of the access device from the opening.

The securing preferably comprises: pushing a lip disposed on a proximal portion of the body of the access device against an outer surface of the wall of the hollow organ; and expanding a balloon disposed on a distal portion of the body to capture the wall between the lip and the balloon.

The securing alternatively comprises: movably disposing a plurality of hooks in the body between exposed and unexposed positions; and actuating the plurality of pins from the unexposed position to an exposed position subsequent to the inserting of the body in the opening to embed the exposed plurality of hooks into the wall. Preferably, the actuating comprises: rotating a portion of the body in a first direction to expose the plurality of hooks; and translating a portion of the body in a second direction to embed the plurality of hooks into the wall. In which case, the removing of the access device from the wall of the hollow organ preferably comprises: translating the translated portion of the body in a direction opposite to that of the second direction to dislodge the embedded plurality of hooks from the wall; and rotating the translated portion of the body in a direction opposite to that of the first direction to unexpose the plurality of hooks.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of procedures and providing access to various hollow organs, it has been found particularly useful in the environment of providing intracardiac access in a beating heart open chest procedure. Therefore, without limiting the applicability of the invention to providing intracardiac access in a beating heart open chest procedure, the invention will be described in such environment.

Figure 1:
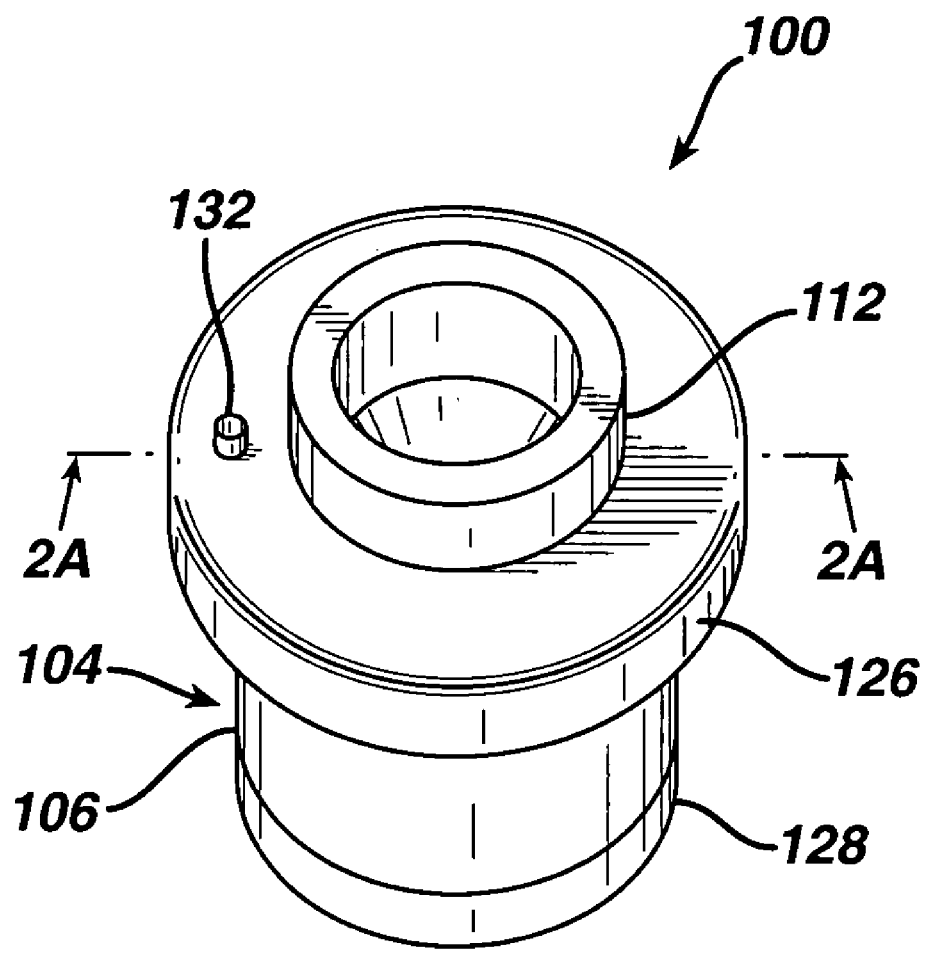
FIG. 1 illustrates an isometric view of a first preferred implementation of an intracardiac access device having an expandable balloon.
Figure 2A:
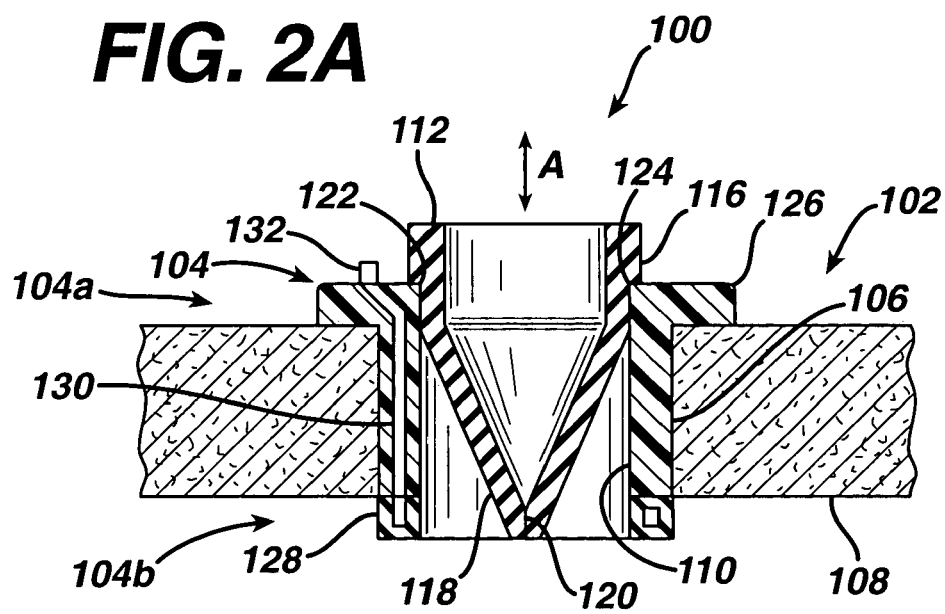
FIG. 2A illustrates a sectional view of the intracardiac access device of FIG. 1 as taken along line 2—2 therein in which the access device is inserted into an opening in a heart wall and the expandable balloon is in a relaxed state.
Figure 2B:
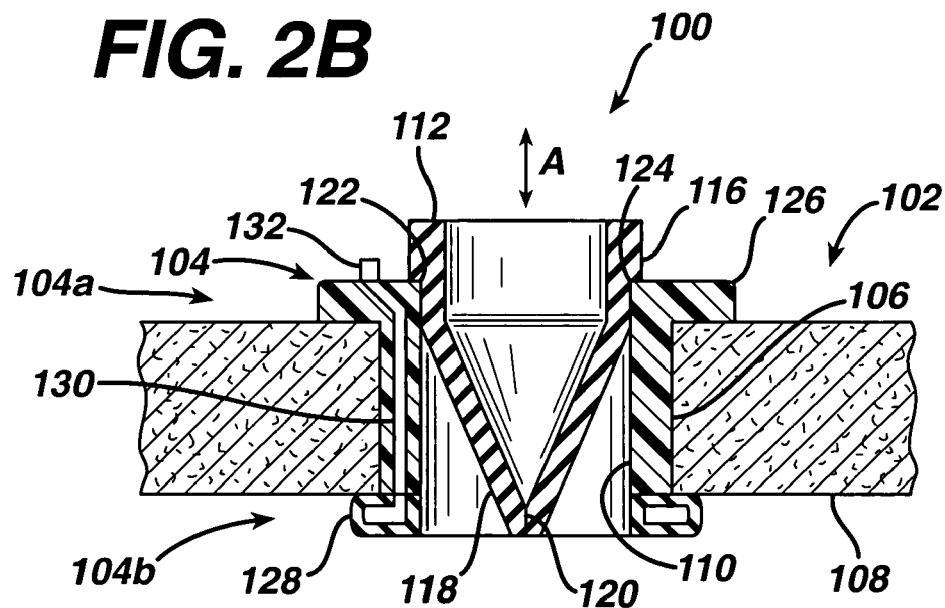
FIG. 2B illustrates the sectional view of FIG. 2A in which the expandable balloon is in an expanded state.

Referring now to FIGS. 1, 2A, and 2B there is shown a first preferred implementation of an intracardiac access device having an expandable balloon, the first preferred implementation of the access device being generally referred to by reference numeral 100. The access device 100 provides access into a hollow organ 102, such as the heart, during an open surgical procedure. The access device has a body 104 that is inserted into an opening or incision 106 in a wall 108 of the hollow organ 102. The body 104 is preferably cylindrical in shape and is typically fabricated from a medical grade thermoplastic and can be fabricated from any methods known in the art, such as conventional machining or injection molding. The body 104 has a bore 110 sized to permit at least a distal portion of an instrument (not shown) to pass through the bore 110 and into an interior of the hollow organ 102. The bore extends in an axial direction A from an exterior of the hollow organ 102 to an interior of the hollow organ 102.

A valve 112 is disposed in the bore 110 of the body 104 for allowing passage of the instrument while substantially preventing a fluid in the interior of the hollow organ 102 from leaking outside the hollow organ 102. Preferably, the valve 112 is what is commonly referred to in the art as a duckbill valve. The duckbill valve 112 is fabricated from an elastomer, such as silicone, and has a cylindrical portion 116 and a tapered portion 118. The tapered portion 118 terminates in a slit 120. The slit 120 is normally closed to provide a seal and is configured to conform to a shape of an instrument passed through the slit 120 to provide a seal around the instrument. The duckbill valve 112 further has a stepped portion 122 that rests on a corresponding shoulder 124 of the body 104. The duckbill valve 112 can be press fit into the body or retained therein by way of a medical grade adhesive. Alternatively, a flange (not shown) can be used to capture a portion of the duckbill valve 112. Although, duckbill valves are preferred, other types of valves known in the art can be used without limiting the scope or spirit of the present invention, such as a flexible membrane (not shown) having a small expandable aperture.

The access device 100 also has securing means for securing the body 104 to the wall 108 of the hollow organ 102. The securing means fixes the body 104 to the wall 108 such that it is not in danger of coming off or falling into the interior of the internal organ 102. Preferably, the securing means also provides a seal between the opening 106 and the body 104 of the access device 100. In a first preferred implementation, the securing means comprises a balloon configuration. In such a configuration, a lip 126, which is preferably cylindrical, is disposed on a proximal portion 104a of the body 104. The lip 126 is preferably integrally formed with the body 104, but may also be formed separately and attached to the body 104 by any means known in the art, such as by ultrasonic welding, thermal welding, or with a medical grade adhesive.

A balloon 128 is disposed on a distal portion 104b of the body 104. The balloon is shown in a deflated or relaxed position in FIG. 2A. The relaxed position of the balloon 128 may be due to the lack of a fluid, such as saline or air, therein, or by applying a vacuum to the balloon. A conduit 130 is preferably formed in the body for supplying the fluid from a fluid source (not shown) or applying a vacuum from a vacuum source (not shown) to the balloon for expansion or contraction, respectively, thereof. A port 132 is preferably provided in fluid communication with the conduit 130 to facilitate connection of the fluid or vacuum source to the conduit 130. Preferably, the fluid and vacuum source comprise a syringe (not shown) and the port 132 comprises a self-sealing needle port as is known in the art. FIG. 2B shows the balloon 128 in an expanded position in which the wall 108 of the hollow organ 102 is captured between the lip 126 and the balloon 128. Although not shown, it is preferred that the wall 108 be compressed slightly upon the expansion of the balloon 128.

Figure 3A:
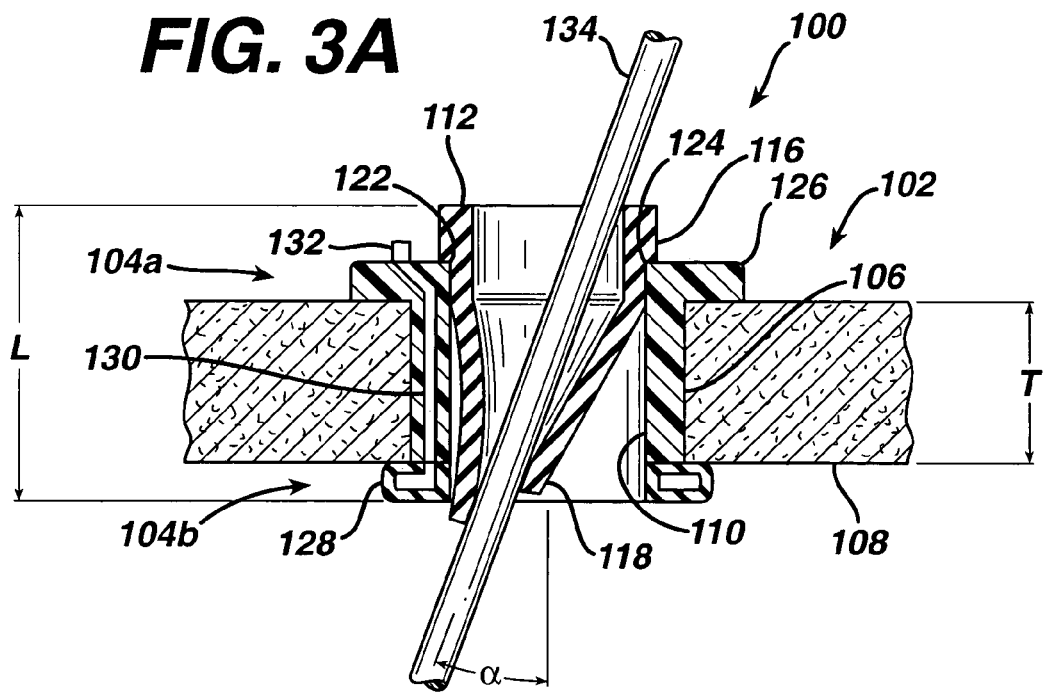
FIG. 3A illustrates the sectional view of FIG. 2B having a straight instrument passed therethrough.
Figure 3B:
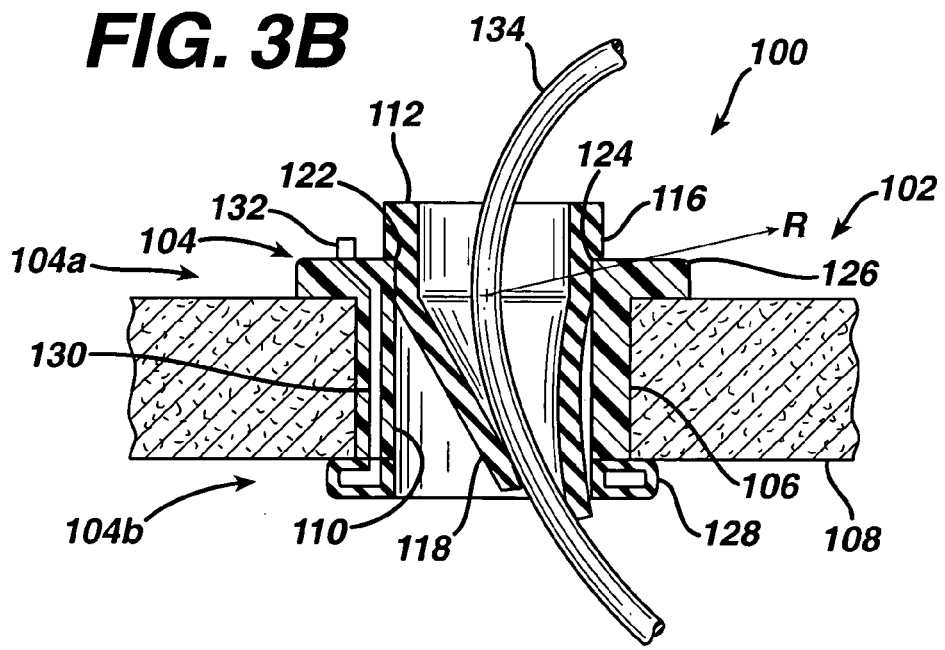
FIG. 3B illustrates the sectional view of FIG. 2B having a curved instrument passed therethrough.

Referring now to FIGS. 3A and 3B, the body 104 has a low-profile length L in the axial direction A of the bore 110 to increase a manipulative capability of the instrument 134 through the bore 110. Preferably, the length L of the body 104 in the axial direction A of the bore 110 is substantially within a range of 1.5T to 5T, where T is a thickness of the wall 108. For example, the thickness for a typical heat wall varies between approximately 3–7mm and the length L of the body 104 is in the range of 4.5 mm to 35 mm, most preferably about 10–15mm.

As clearly seen in FIG. 3A, the low-profile length L of the body 104 as compared to the thickness T of the wall 108 allows an instrument 134 to be manipulated at a greater angle α with respect to a central axis of the bore than the endoscopic access devices of the prior art. Furthermore, as clearly shown in FIG. 3B, the low-profile length L of the body 104 as compared to the thickness T of the wall 108 allows insertion of a curved instrument having a radius R, which is not possible with the endoscopic access devices of the prior art.

Figure 4:
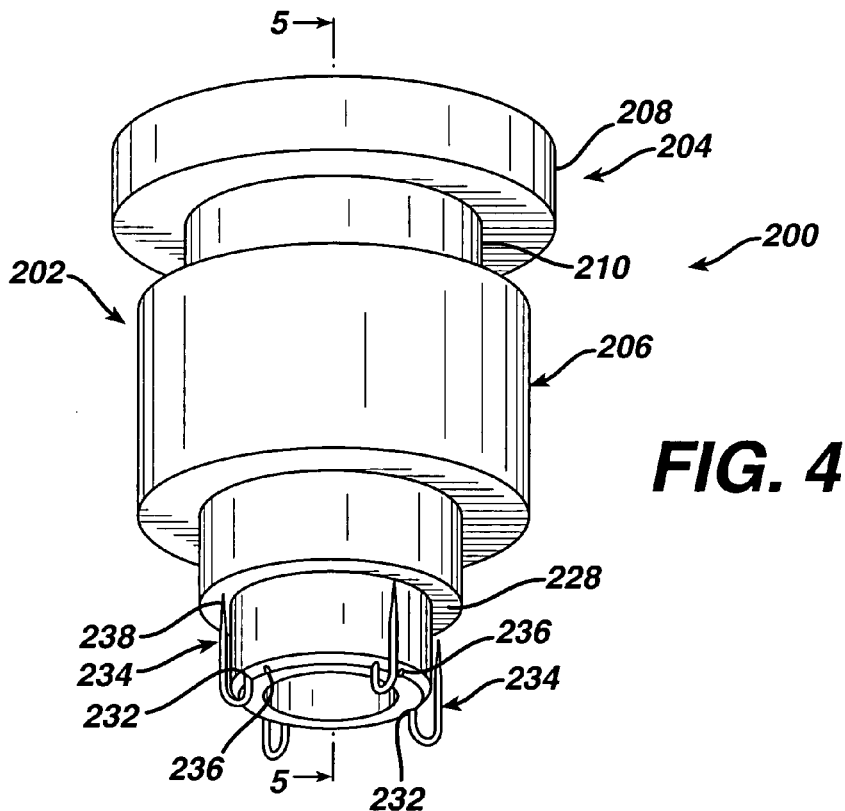
FIG. 4 illustrates an isometric view of a second preferred implementation of an intracardiac access device having a plurality of hooks, the hooks being shown in an exposed position.
Figure 5:
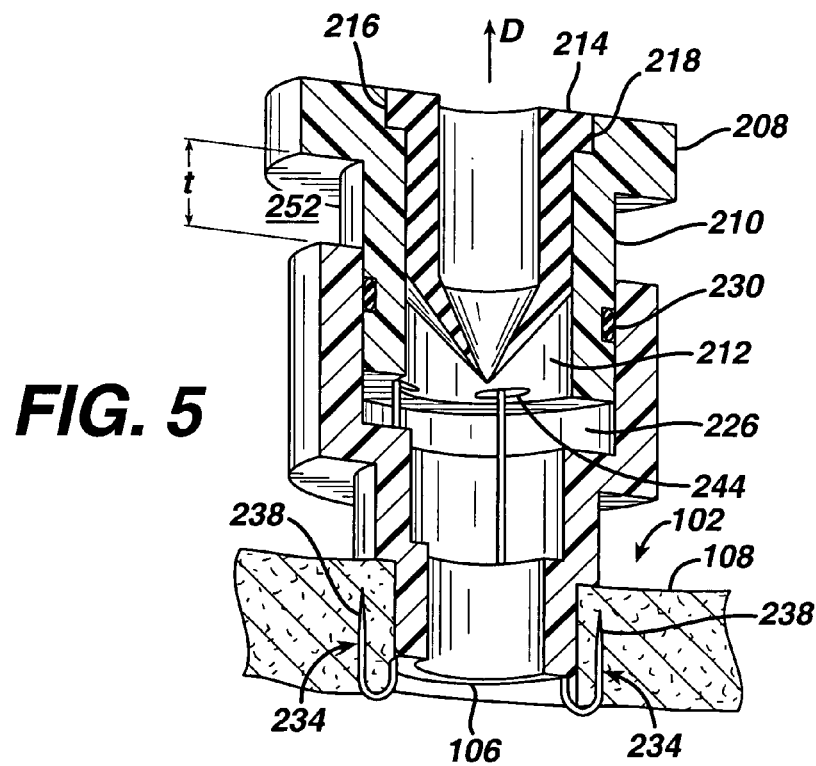
FIG. 5 illustrates a sectional view of the access device of FIG. 4 as taken along line 5—5 in FIG.
Figure 11:
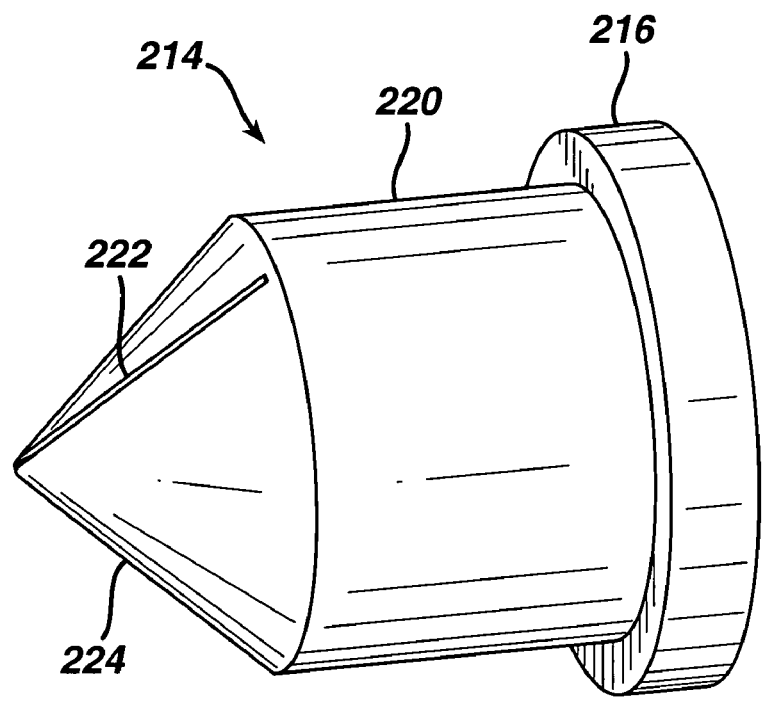
FIG. 11 illustrates a preferred implementation of a valve for use with the access device of FIG. 4.

Referring now to FIGS. 4 and 5, there is illustrated a second preferred implementation of an access device of the present invention, the second preferred access device being generally referred to by reference numeral 200. Access device 200 also preferably has a low-profile shape as discussed above with regard to the first preferred implementation and has the same advantages as discussed above with regard to FIGS. 3A and 3B. Access device 200 includes a body 202 having first and second body portions 204, 206, respectively. The first and second body portions 204, 206 are fabricated from any medical grade material, such as stainless steel or a polymer. The first body portion 204 includes a flange 208 and a cylinder portion 210. The first body portion 204 further has a bore 212 that accommodates a valve 214. Referring now to FIG. 11, the valve 214 is preferably a duckbill or slit valve fabricated from a medically approved elastomer, such as silicone. The valve 214 has a flange 216 which fits within a corresponding stepped groove 218 in the bore 212 of the first body portion 204. The valve 214 also has a cylindrical body portion 220 that fits within the bore 212 of the first body portion 204. The valve 214 has a slit 222 on a conical nose 224 thereof to sealingly accommodate an instrument inserted through the access device 200. The valve 214 is retained in the bore 212 by any means known in the art such as by adhesive or press-fit. The valve 214, although shown disposed in the first body portion 204 may also be disposed in the second body portion 206 and although shown and described as a discrete part may be integrally formed with either of the first and second body portions 204, 206.

Referring back to FIGS. 4 and 5, the second body portion 206 has a bore 226, at least a portion of which accommodates the cylinder portion 210 of the first body portion 204 such that it is free to both rotate and translate within the bore 226 of the second body portion 206. The second body portion 206 further has at least one shoulder or flange 228 on an exterior surface thereof. A seal, such as an o-ring 230 is provided to seal a fluid path between the first and second body portions 204, 206. The second body portion 206 further has a plurality of first longitudinal channels 232 corresponding to each of a plurality of hooks 234 disposed circumferentially about the second body portion 206. Each of the plurality of hooks 234 have at least a portion thereof which is slidingly disposed in a corresponding first longitudinal channel 232. The second body portion also includes a plurality of second longitudinal channels 236 for housing an upturned portion 238 of the hooks 234 when the hooks 234 are in an unexposed position.

Figure 10:
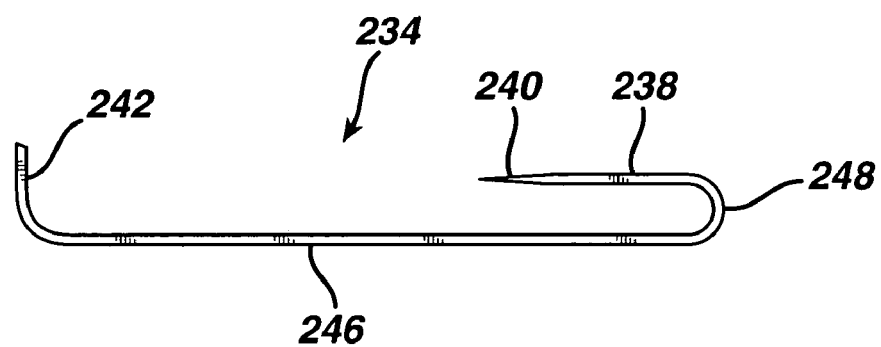
FIG. 10 illustrates a side view of a preferred implementation of one of the plurality of hooks for use with the access device of FIG. 4.

Referring now to FIG. 10, one of the plurality of hooks 234 is shown therein. The hooks 234 are fabricated from a medically approved metallic material, such as stainless steel and have a sharp pointed end 240 at the end of the upturned portion 238. At a proximal end of the hook is a tuned-in portion 242 that engages with and is retained in portions of the first body portion 204, such as in corresponding circumferential slots 244 in the bore 212 of the cylinder portion 210. At the distal end of the hooks 234 is the upturned portion 238. A straight portion 246 connects the in-turned 242 and upturned 238 portions with a curved portion 248 at a transition between the straight portion 246 and the upturned portion 238. At least a portion of the straight portion 246 is slidingly disposed in a corresponding first longitudinal channel 232.

Figure 6:
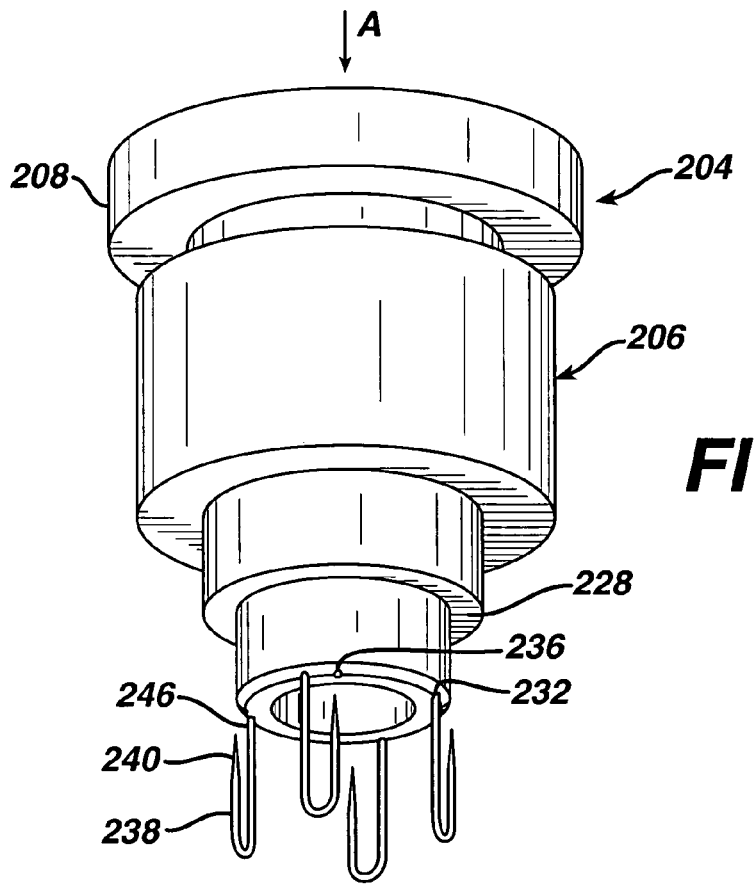
FIG. 6 illustrates an isometric view of the access device of FIG. 6 with the plurality of hooks being rotated while in an extended position.
Figure 7:
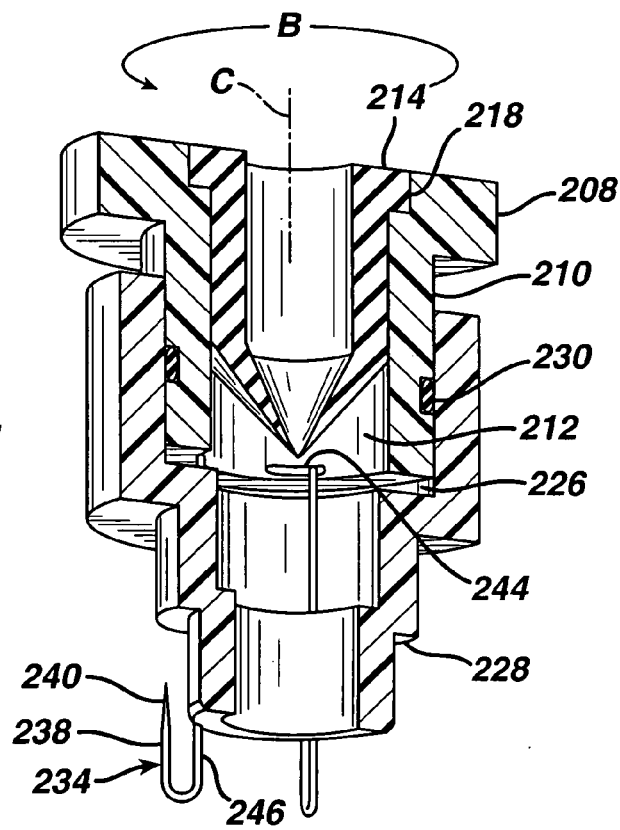
FIG. 7 illustrates a sectional view of the access device of FIG. 4 with the plurality of hooks being in an extended position.
Figure 8:
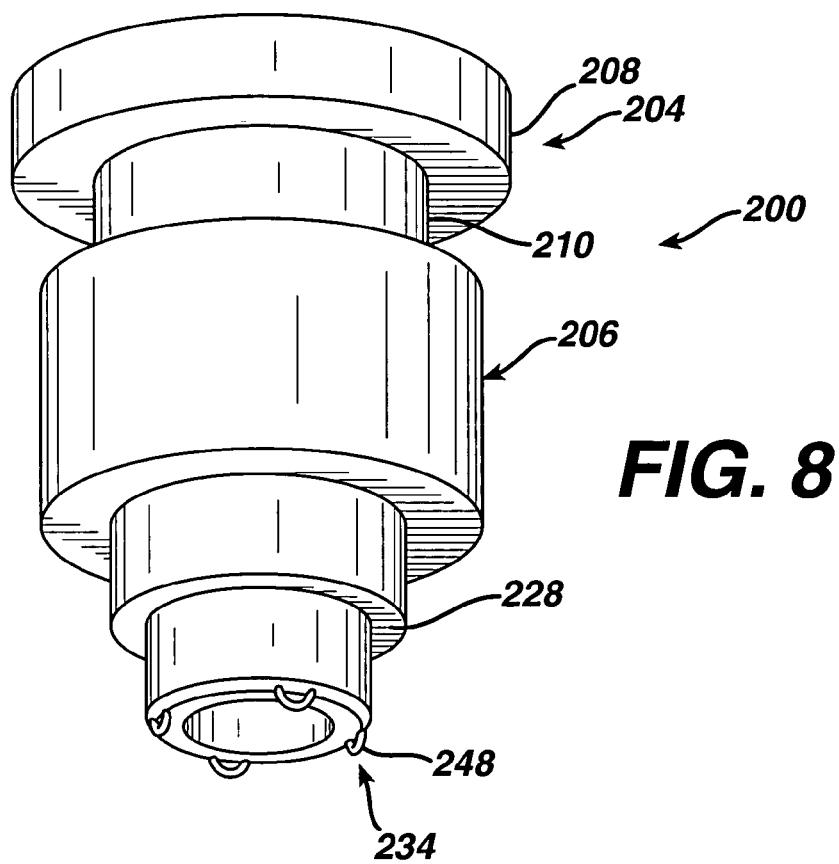
FIG. 8 illustrates an isometric view of the access device of FIG. 7 with the plurality of hooks in the unexposed position.

Referring now to FIGS. 5–8, an operation of the access device 200 of the second preferred implementation will be described. The access device 200 is securely positioned in an incision 106 in a wall 108 of a hollow organ 102, such as the heart. The incision is made by any methods known in the art and may be a slit or a punched hole after access is provided to the hollow organ, such as by a gross thoracotomy. The wall 108 is shown in FIG. 5, but omitted from FIGS. 6–8 for the sake of clarity. Referring first to FIG. 8, the upturned portions 238 of the hooks 234 are disposed in corresponding second longitudinal channels 236 such that the sharp pointed ends 240 are unexposed. The access device is inserted into the incision 106 while the hooks 234 are in the unexposed position as shown in FIG. 8. While the upturned portions 238 are shown as being disposed in the second longitudinal channels 236 in the unexposed position, they can alternatively be disposed in corresponding cut-outs (not shown) on the exterior of the second body portion 206.

Figure 9:
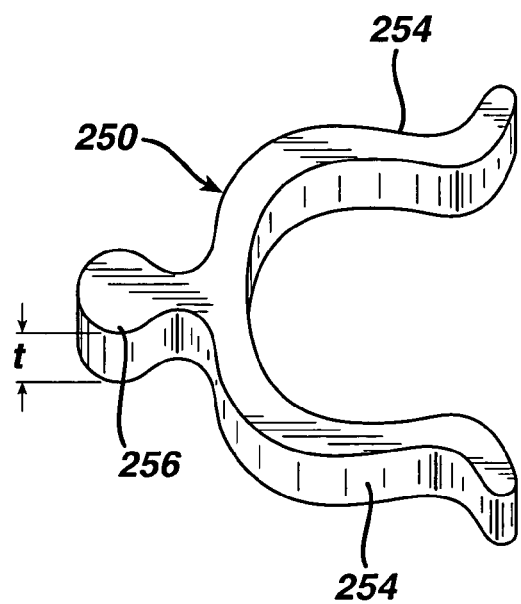
FIG. 9 illustrates an isometric view of a spacer for use with the access device to lock the same with the hooks in the exposed position.

Referring next to FIG. 6, the first body portion 204 is translated relative to the second body portion 206 in the direction of arrow A to extend the upturned portions 238 from the second longitudinal channels 236. Referring now to FIG. 7, the first body portion 204 is then rotated in the direction of arrow B about a central axis C to turn the upturned portions 238 90 degrees and expose the sharp pointed ends 240. When the first body portion 204 is rotated, the hooks 234 are rotated by an interference with the in-turned portions 242 of the hooks 234 and a wall of the corresponding slots 244. Once the hooks 234 are both extended and exposed as shown in FIG. 6, the first body portion 204 is translated in the direction of arrow D (opposite to the direction of arrow A) to embed the upturned portions 238 into the wall 108 of the hollow organ 102 circumferentially about the incision 106, as shown in FIG. 5. The access device 200 is then secured to the wall 108 by sandwiching the wall 302 between the step or flange 228 and the curved portions 248 of the hooks 234. Referring now to FIGS. 5 and 9, while the hooks 234 are embedded into the wall 108, a locking clip 250 is disposed in a gap 252 between the flange 208 of the first body portion 204 and the second body portion 206 to prevent any translation of the first body portion 204 in the direction of arrow A. The thickness t of the locking clip 250 substantially conforms to a thickness t of the clip. The locking clip 250 is preferably fabricated from a medically approved polymer and has fingers 254 which elastically deform to fit within the gap 252. The locking clip 250 further has a pull 256 for facilitating handling and inserting and removing the locking clip 250 into and from the gap 252. Locking clip 250 may have a tether attached to it on one end and to a point outside the operative field on another end to prevent locking clip 250 from inadvertently being left within the patient when the procedure is complete. Alternatively, the locking clip 250 may be tethered to the access device 200 itself. While the access device 200 is secured and locked to the wall 108, surgical instruments (not shown) are inserted through the valve such that the working ends thereof are inserted into an interior of the hollow organ for performing a necessary surgical procedure.

After completion of the surgical procedure, the access device 200 is removed and the incision 106 is closed. To remove the access device 200 from the incision 106, the clip 250 is removed and the first body portion 204 is translated in the direction of arrow A to dislodge the upturned portions 238 of the hooks 234 from the wall 108. The first body portion 204 is then rotated in a direction opposite to that of arrow B about the central axis C to rotate the hooks 90 degrees such that the sharp pointed ends 240 are aligned with the second longitudinal channels 236. The first body portion 204 is then translated in the direction of arrow D to return the up-turned portions 238 of the hooks 234 to the unexposed positions in the second longitudinal channels 236. The access device 200 is then removed from the incision 106 and the incision 106 is closed by any means known in the art, such as with sutures or surgical glue.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An access device for providing access into a hollow organ during an open surgical procedure, the access device comprising:
    a body for insertion into an opening in a wall of the hollow organ, the body having a bore for passage of at least a distal portion of an instrument into an interior of the hollow organ and a lip configured to contact a wall of the hollow organ;
    a non-quadranted valve disposed in the bore and configured for allowing passage of the instrument into the interior of the hollow organ and substantially preventing a fluid in the interior of the hollow organ from leaking outside the hollow organ; and
    securing means comprised of the lip disposed on a proximal portion of the body, a balloon disposed on a distal end of the body, a conduit for supplying a fluid from a fluid source to the balloon for expansion thereof, the securing means configured for contactingly securing the wall of the hollow organ therebetween the lip and the balloon upon expansion of the balloon;
    wherein the body has a low-profile length relative to the thickness of the wall in an axial direction of the bore.

2. The access device of claim 1, wherein the length of the body in the axial direction of the bore is substantially within a range of 1.5T to 5T, where T is a thickness of the wall.

3. The access device of claim 1, wherein the valve is a duckbill valve fabricated from an elastomer.

4. The access device of claim 3, wherein the elastomer is silicone.

5. The access device of claim 1, wherein the body, lip, and balloon are cylindrical.

6. The access device of claim 1, wherein the hollow organ is a heart.

* * * * *